(12) United States Patent
Drevik

(10) Patent No.: US 6,315,766 B1
(45) Date of Patent: Nov. 13, 2001

(54) SANITARY NAPKIN HAVING IMPROVED SIDE LEAKAGE PROTECTION

(75) Inventor: Solgun Drevik, Mönlycke (SE)

(73) Assignee: SGA Hygiene Products Aktiebolag, Gothenberg (SE)

( * ) Notice: Subject to any disclaimer, the term of this patent is extended or adjusted under 35 U.S.C. 154(b) by 0 days.

(21) Appl. No.: 09/051,824

(22) PCT Filed: Oct. 22, 1996

(86) PCT No.: PCT/SE96/01350

§ 371 Date: Apr. 2, 1998

§ 102(e) Date: Apr. 2, 1998

(87) PCT Pub. No.: WO97/15259

PCT Pub. Date: May 1, 1997

Related U.S. Application Data

(63) Continuation of application No. 09/051,284, filed on Apr. 2, 1998.

(30) Foreign Application Priority Data

Oct. 25, 1995 (SE) .................................................. 9503751

(51) Int. Cl.[7] .................................................... A61F 13/15
(52) U.S. Cl. ................... 604/387; 604/386; 604/385.04; 604/385.22
(58) Field of Search ................ 604/385.1, 386, 604/387, 385.04, 385.22

(56) References Cited

U.S. PATENT DOCUMENTS

| | | | |
|---|---|---|---|
| 4,758,241 | * | 7/1988 | Papajohn .............................. 604/387 |
| 4,897,084 | * | 1/1990 | Ternstrom et al. ................ 604/385.1 |
| 4,917,697 | * | 4/1990 | Osburn et al. ........................ 604/387 |
| 5,037,417 | * | 8/1991 | Ternström ............................. 604/387 |
| 5,098,422 | * | 3/1992 | Davis et al. .......................... 604/387 |
| 5,125,918 | * | 6/1992 | Seidy .................................... 604/387 |
| 5,129,893 | * | 7/1992 | Thoren .............................. 604/385.4 |
| 5,133,705 | * | 7/1992 | Nakanishi et al. ................... 604/387 |
| 5,221,275 | * | 6/1993 | Van Iten ............................... 604/387 |
| 5,275,591 | * | 1/1994 | Mavinkurve .................... 604/385.04 |
| 5,344,416 | * | 9/1994 | Niihara ........................... 604/385.04 |
| 5,346,486 | * | 9/1994 | Osburn et al. ................. 604/385.04 |
| 5,391,162 | * | 2/1995 | Widland et al. ................ 604/385.04 |
| 5,591,147 | * | 1/1997 | Couture-Dorschner et al. ................. 604/385.04 |

FOREIGN PATENT DOCUMENTS

| | | |
|---|---|---|
| 0 330 206 A1 | 8/1989 | (EP) . |
| WO 95/17148 | 6/1995 | (WO) . |

* cited by examiner

*Primary Examiner*—John G. Weiss
*Assistant Examiner*—Michael Bogart
(74) *Attorney, Agent, or Firm*—Burns, Doane, Swecker & Mathis, L.L.P.

(57) ABSTRACT

A sanitary napkin includes an absorbent body enclosed between an outer, liquid-impermeable casing sheet and an inner liquid-permeable casing sheet that lies proximal to the wearer's body when the napkin is in use; two side-bodies disposed laterally outside the side-edges of the absorbent body on both sides thereof, at least in the central part of the napkin, the side-bodies being separate from the absorbent body and joined to at least the outer casing sheet; and a pre-stretched elastic extending transversely between the two side-bodies which is disposed exterior to the outer casing sheet and distal to the wearer's body when the napkin is in use. The pre-stretched elastic extends laterally outside the absorbent body on both sides thereof and is attached at portions thereof to at least one of the outer casing sheet and the side-bodies.

10 Claims, 2 Drawing Sheets

SANITARY NAPKIN HAVING IMPROVED SIDE LEAKAGE PROTECTION

CROSS REFERENCE RELATED APPLICATIONS

The present application is a continuing prosecution application of Ser. No. 09/051,284, filed on Apr. 2, 1998, which is a national stage application of PCT International Application No. PCT/SE96/01350, filed on Oct. 22, 1996, and which was published in English on May 1, 1997.

TECHNICAL FIELD

The present invention relates to a sanitary napkin which comprises an absorbent body enclosed between an outer liquid-impermeable casing sheet and an inner liquid-permeable casing sheet which lies proximal to the wearer's body in use.

BACKGROUND OF THE INVENTION

One problem associated with the construction of sanitary napkins is ensuring that the napkins offer protection against leakage. The main reason why sanitary napkins leak is not because their absorption capacity is insufficient, but because the liquid or fluid discharged from the wearer is either deposited onto one side of the absorbent body or runs along its surface without being absorbed, either because the napkin has been incorrectly positioned when donned or because the napkin has been deformed by the forces exerted on the napkin when in use, among other things. Swedish Patent Application No. 9402448-6 discloses a sanitary napkin with which this problem is solved by placing beneath the absorbent body a compressible and resilient layer of material which functions to press the absorbent body resiliently against the wearer's body when the napkin is worn. A sanitary napkin of this kind has been found to be extremely reliable against leakage. However, the resilient layer must be relatively thick in order to ensure that it will function effectively, and consequently this solution is not suited for application with thin sanitary napkins, i.e. sanitary napkins having a total thickness of less than 5 mm.

SUMMARY OF THE INVENTION

It is also known to attach transversely directed elastic means to the underside of an absorbent body in order to deform the body to have a convex shape as seen in a cross section, see for example EP-A1-0 330 206.

The object of the present invention is to enable sanitary napkin to be made lockproof in a manner which can also be applied to thin sanitary napkins and therewith solve the aforesaid problem.

This object is achieved in accordance with the invention with a sanitary napkin of the aforesaid kind which is characterized in the sanitary napkin includes two separate side-bodies which extend along the outside of the side-edges of the absorbent body on both sides thereof, at least in the central part of the sanitary napkin, and are joined to at least the outer casing sheet, and also pre-stretched elastic devices which strive to move the side-edges of the side-bodies distal from the absorbent body towards one another on that side of the sanitary napkin which lies distal from the wearer in use. Such side-bodies will act as resilient spacing elements which, when the napkin is worn, press the central part of the napkin resiliently into contact with the wearer's body and therewith ensure effective protection against leakage.

In one preferred embodiment, the side-bodies are enclosed between the two casing sheets. The absorbent body also has an hourglass configuration and the side-bodies extend longitudinally in the region of the inwardly curved concave parts thereof. The side-bodies have a shape which corresponds to the shape of respective concave parts of the absorbent body. In one preferred variant, the elastic devices have the form of a piece of elastic material which extends transversely between the side-bodies and the side-edges of which are either fastened to said side-bodies or to parts of the outer casing sheet joined to said bodies. In another variant, the elastic devices have the form of transverse elastic threads or bands which extend transversely between the side-bodies and the ends of which are fastened to said side-bodies or to parts of the outer casing sheet joined thereto. The side-bodies preferably have the shape of a segment of a circle, although it is conceivable to curve the side-edges of the side-bodies distal from the absorbent body in directions opposite to the side-edges that lie proximal to the absorbent body. The elastic devices are pre-stretched so that when the sanitary napkin is in a load-free state, the side-bodies will be maintained in a plane which defines an obtuse angle with the plane of the absorbent body and the rigidity or stiffness of the side-bodies is sufficient to enable said bodies to withstand the loads that normally occur when the napkin is in use, essentially without being deformed. In one variant, the side-bodies may be made of a resilient material.

BRIEF DESCRIPTION OF THE DRAWINGS

The invention will now be described in more detail with reference to the accompanying drawings, in which FIG. 1 and 2 illustrate from above a first embodiment of an inventive sanitary napkins, wherein FIG. 1 shows the side of the napkin that lies proximal to the wearer's body in use and FIG. 2 shows the side of the napkin that lies distal to the wearer's body in use, the napkin being shown in a flat state;

DETAILED DESCRIPTION OF THE INVENTION

Figure 1:
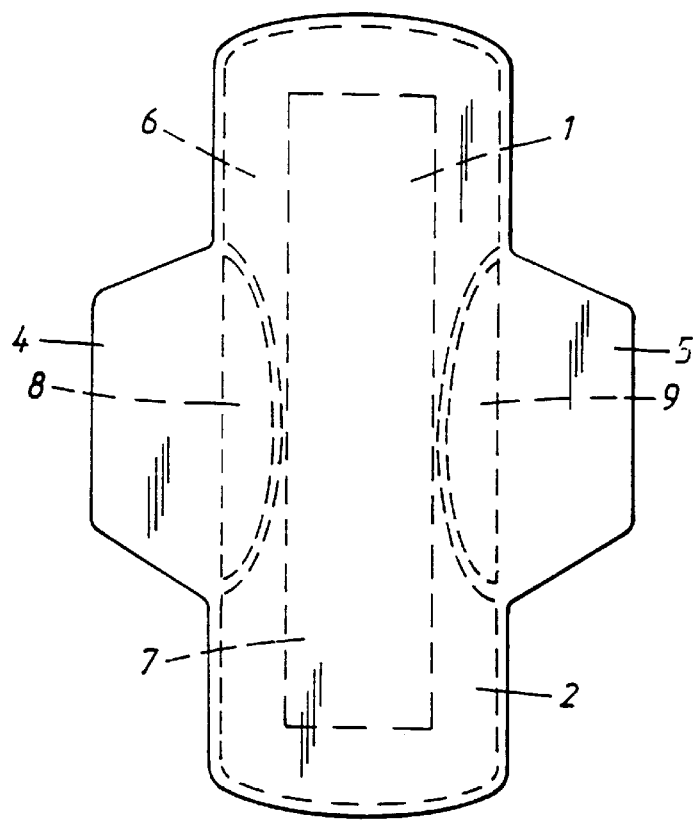

The sanitary napkin illustrated in FIG. 1–4 is comprised of a thin absorbent body 1, preferably having a thickness of 2–5 mm, which is enclosed between an inner liquid-permeable casing sheet 2, e.g. a sheet of non-woven material, perforated plastic film or the like, and an outer liquid-impermeable casing sheet 3, made for instance of polyethylene. The casing sheets, 2,3 extend peripherally slightly beyond the absorbent body 1 and are there joined together. The two casing sheets form in the crotch part of the sanitary napkin flaps or wings 4,5 which are intended to be folded around respective edges of the wearer's panties and fastened to the outside thereof.

The absorbent body 1 includes a first hourglass-shaped layer 6 of air-laid cellulose fluff which is disposed nearest the liquid-permeable casing sheet 2. Provided between the layer 6 and the outer liquid-impermeable casing sheet 3 is a rectangular second layer 7 which is joined to the casing sheet, e.g. by a glue bead. In the illustrated embodiment, this second layer is comprised of an absorbent structure that includes a dry-formed sheet contain 5–100% cellulose fibers and formed by compressing a cellulose-fiber containing web without subsequent defibration and fluffing. Such absorbent structures are described in International Patent Applications PCT/SE 93/00971-00975, to which the reader is referred for a some detailed description of such material. In addition to imparting good absorption properties to the absorbent body 1, the second layer 7 also stiffens the absorbent body.

According to the invention, the sanitary napkin includes two side-bodies 8, 9 which are enclosed between the casing sheets 2, 3 around the whole of their peripheries and are placed laterally outside the absorbent body 1 within its central region. In the illustrated embodiment, the side-bodies have a shape which is complementary to the inwardly curved or concave parts of the hourglass layer 6. Extending transversely across the sanitary napkin is a pre-stretched piece 10 of elastically resilient material, for instance plastic film having a so-called elastic memory, which extends over the central part of the napkin with its side-edges located in the region of the side-bodies. The side-edges of the elastic piece are either fastened to the liquid-impermeable casing sheet 3, e.g. glued thereto, or are fastened indirectly to the side-bodies by a weld join that joins the elastic piece 10 to the casing sheets 2, 3. When the side-bodies are comprised of fiber material, thermoplastic fibers or the like may be mixed with the fiber material to enable the outer casing sheet and the elastic piece to be welded to the side-bodies.

Figure 2:
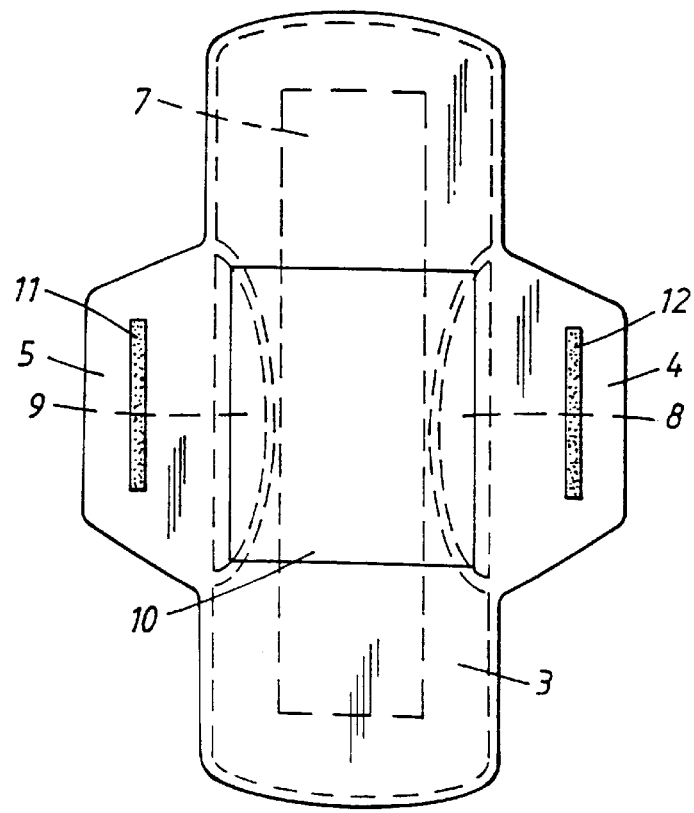

FIG. 1 and 2 show the sanitary napkin in the flat state of the napkin after manufacture and prior to folding the napkin for packaging purposes.

Figure 3:
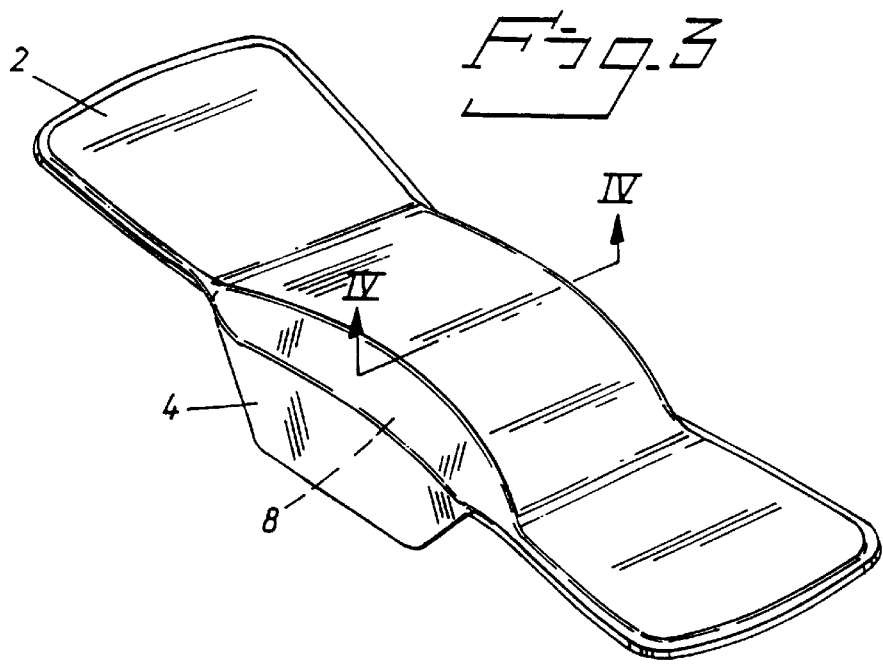
FIG. 3 illustrates the sanitary napkin according to the first embodiment in the absence of load on the napkin.
Figure 4:
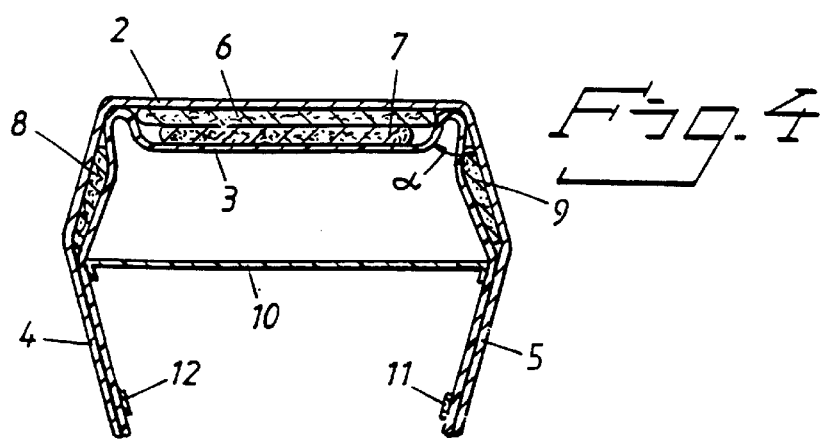
FIG. 4 is a cross-sectional view taken on the line IV—IV in FIG. 3.

FIG. 3 and 4 show the sanitary napkin in the absence of load thereon, i.e. in the state when removed from its packet. In the absence of load on the sanitary napkin, the pre-stretched elastic piece 10 will have contracted and therewith swung the side-bodies 8, 9 so that they face downwards. At the same time, the absorbent body is curved so that the central region of the absorbent body will have an upwardly convex shape when seen from one side.

The sanitary napkin is secured in the panties of a wearer, by folding the wings 4 and 5 in over the underside of the panties and fastening the wings of the napkin thereto with the aid of glue beads 11, 12 provided on the wings to this end. The sanitary napkin is dimensioned so that the wings must be drawn laterally outwards from the downwardly projecting position shown in FIG. 3 and 4 in order to be able to fold the wings around the edges of a pair of panties of conventional size and make. As the wings are pulled, the elastic piece 10 will be stretched and the side-bodies swung up from the position shown in FIG. 4, therewith reducing the curvature of the central, upwardly convex part of the absorbent body. When donning a pair of panties with a sanitary napkin fitted thereon in the aforesaid manner, the elastically resilient piece of material will endeavor to contract to the state shown in FIG. 4, although such contraction is counteracted by abutment of the sanitary napkin with the wearer's body and the napkin cannot be curved out of contact with the body. An applied sanitary napkin will thus be pressed resiliently against the wearer's body.

The outer edges of the side-bodies form natural fold indications when fitting the aforedescribed sanitary napkin, so that when placing the sanitary napkin in a pair of panties, the user will fold those parts of the casing sheets that lie laterally outside the side-bodies in against the underside of the panties. Furthermore, the positioning which the elastic piece 10 is attached is such that when the sanitary napkin is in a load-free state, the aforesaid folding indications will be clearly seen by virtue of the wings defining an angle with the side-bodies, as will be seen from FIG. 4. It may be suitable to make the side-bodies or the absorbent body resiliently deformable. This can be achieved, for instance, by constructing the side-bodies from an elastic foam material or by causing the absorbent body to coact with a layer of elastic foam material, for instance by forming the layer 7 from such material.

When the sanitary napkin is in use, the end-parts of the napkin are able to move transversely when said parts include a rigid, non-bendable material. To facilitate movement of said end-parts, it may be appropriate to refrain from the glue strings or the like that are typically provided on the end-parts of a sanitary napkin for affixing the napkin to the wearer's panties. However, it may be appropriate to provide the end-parts with a friction coating to prevent the end-parts moving sideways in relation to the panties. When the sanitary napkin includes rigid, bendable material or soft material in the end-parts of the napkin, glue strings or the like may be applied both on the front and the rear end-part.

The inventive concept can also be applied to a wingless sanitary napkin, which is principle the same as the afore-described sanitary napkin with the exception of having no wings. In this latter application, glue strings or beads are preferably provided along the side-edges of the outer casing sheet in the region of the side-bodies, for fastening the napkin to the wearer's panties. In one variant, which is not a preferred variant, a glue string or the like may instead be provided on the outer casing sheet of at least one of the end parts of the napkin for fastening the napkin to the wearer's panties. However, in the case of this variant a fastening agent is preferably provided on both end parts of the napkin, wherein curving and flattening of the central part is made possible by bending deformation of the napkin end-parts, provided that the central part of the napkin is essentially free from load when the end-parts are affixed. Such bending deformation can be accepted in the end-parts, particularly in the front end-part, since there is little risk that deformation of these parts will result in leakage of the sanitary napkin.

In order to ensure that external loads on an inventive sanitary napkin will not cause the side-bodies 8, 9 to be swung inwards and folded-in beneath the absorbent body, the angle α between the plane of the absorbent body and the plane of the side-bodies shall be greater than or equal of 90° when the sanitary napkin is in the load-free state shown in FIG. 3 and 4. This is particularly important in the case of an inventive wingless sanitary napkin which is fastened to the wearer's panties at the end-parts of the napkin.

The side-bodies will preferably be made of a relatively rigid material, so that external loads on the napkin will cause the side-bodies to swing outwards and the elastic piece 10 to stretch, without deforming the side-bodies.

Figure 5:
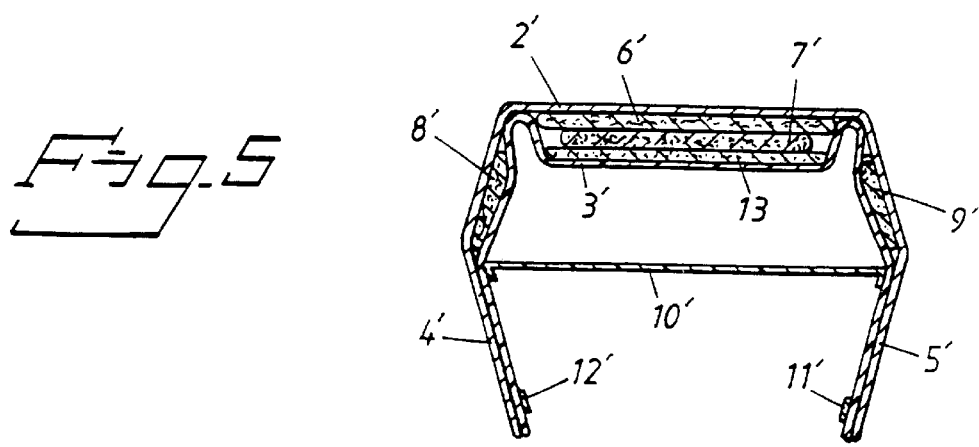
FIG. 5 is a cross-sectional view similar to the view of FIG. 4 and illustrating a second embodiment of the invention.

The side-bodies will also preferably be so thin as not to project up beyond the absorbent body when the napkin is in the flat state shown in FIG. 1 and 2. The side-bodies may be made of an absorbent or non-absorbent material and are preferably fastened to at least the outer casing sheet. The side-bodies must be bendable in the plane of said bodies, so that the side-bodies are able to follow the contours of the concave parts of the hourglass layer 6 without any appreciable bending resistance as the side-bodies are swung downwards. Suitable side-body materials includes wadding, foam and FIG. 5 illustrates another embodiment of an inventive sanitary napkin. The FIG. 5 embodiment differs from the aforegoing embodiment by virtue of a reinforcing layer 13 positioned beneath the absorbent body 6', 7'. Those napkin components of the FIG. 5 embodiment that find correspondence in the FIG. 4 embodiment have been identified with the same reference signs to which a prime has been added. In the FIG. 5 embodiment, the side-bodies are made of the same material as the reinforcing layer 13, for instance plastic foam. One advantage afforded by the FIG. 5 embodiment is that the materials included in the absorbent body can be chosen solely with respect to their absorbent properties without paying attention to their stiffness.

It will be understood that the aforedescribed embodiment of the sanitary napkin can be modified within the scope of the invention. For instance, the absorbent body may be constructed of more or fewer than two layers and may comprise other absorbent materials and include layers which either do or do not contain superabsorbents. The piece of elastic material 10 may be replaced with other elastic devices, for instance elastic threads or elastic bands optionally carried by a carrier layer. Neither need the elastic have the illustrated longitudinal extension, but may comprise a single centrally positioned elastic thread, for instance. The direct or indirect fastening of the elastic to the side-bodies may, in principle, be located anywhere between the inner and outer side-edges of the side-bodies. The side-bodies may also have a shape different to that shown and need not have the same lateral extension as the concave parts of the hourglass-shaped layer. However, the illustrated embodiment is preferred because it ensures that external loads will be taken-up essentially by swinging of the side-bodies within the limits of their range of swing. The absorbent body or the layer coacting therewith need not have an hourglass configuration or include concave-shaped recesses, but may have straight side-edges. The outer side-edges of the side-bodies need not be straight as in the illustrated embodiment, but may be curved in directions opposite to the inner side-edges. Neither need the side-bodies be enclosed by casing sheets, and the casing sheets or one of said sheets need only extend laterally over a part of the side-bodies, in which case it is necessary to fasten the side-bodies to at least one of the casing sheets. When a stiffening layer is provided beneath the absorbent body, as in the FIG. 5 embodiment, the side-bodies can be produced by providing fold lines in the stiffening layer. When this stiffening layer is made from a liquid-impermeable material, said layer may replace the outer casing sheet. The invention is therefore only limited by the contents of the following Claims.

What is claimed is:

1. A sanitary napkin comprising:

an absorbent body enclosed between an outer, liquid-impermeable casing sheet and an inner liquid-permeable casing sheet capable of lying proximal to a wearer's body when the sanitary napkin is in use, said absorbent body defining a side edge on each lateral side thereof, two side-bodies disposed laterally outside the side-edges of the absorbent body, one of said side-bodies being disposed laterally outside of each of said edges of the absorbent body, at least in the central part of the napkin, said side-bodies being separate from the absorbent body and joined to at least the outer casing sheet, and a pre-stretched elastic extending transversely between said two side-bodies, said pre-stretched elastic being disposed exterior to the outer casing sheet and which is disposed for lying distal to a body facing side of the sanitary napkin when the sanitary napkin is in use, said pre-stretched elastic extending laterally outside the absorbent body on both sides thereof, with only opposing lateral ends of the pre-stretched elastic being attached to at least one of the outer casing sheet and the side-bodies, such that the locations of attachment are between lateral side edges of the side-bodies.

2. A sanitary napkin according to claim 1, wherein the side-bodies are enclosed between said outer, liquid-impermeable casing sheet and said inner liquid-permeable casing sheet.

3. A sanitary napkin according to claim 1, wherein the absorbent body has an hourglass configuration including an inwardly concave part on each of said side edges thereof; the side-bodies extend longitudinally in a region of the inwardly concave parts of the absorbent body; and the side-bodies have a shape corresponding to a shape of said inwardly concave parts.

4. A sanitary napkin according to claim 1, wherein the pre-stretched elastic comprises an elastic piece of material which extends transversely between he side-bodies; and wherein side-edges of said elastic piece of material are fastened to the side bodies or to parts of the outer casing sheet joined to said side-bodies.

5. A sanitary napkin according to claim 1, wherein said pre-stretched elastic is comprised of transverse elastic threads or elastic bands which extend transversely between the side-bodies and wherein lateral ends of said elastic threads or elastic bands are fastened to said side-bodies or to parts of the outer casing sheet joined to said side-bodies.

6. A sanitary napkin according to claim 1, wherein the side-bodies are segmental in shape.

7. A sanitary napkin according claim 1, wherein the pre-stretched elastic is pre-stretched such that when the sanitary napkin is in a load-free state, the side-bodies are held in a plane that defines with the plane of the absorbent body an angle which is greater than or equal to 90°.

8. A sanitary napkin according to claim 1, wherein the side-bodies have a stiffness such as to be able to withstand those loads that occur in normal use of the napkin, essentially without being deformed.

9. A sanitary napkin according to claim 1 wherein the side-bodies are made of resilient material.

10. A sanitary napkin according to claim 1, wherein the side-bodies define resilient spacing elements which urge the central part of the napkin resiliently into contact with the wearer's body when the napkin is in use to ensure effective protection against leakage.

* * * * *

UNITED STATES PATENT AND TRADEMARK OFFICE
CERTIFICATE OF CORRECTION

| | | |
|---|---|---|
| PATENT NO. | : 6,315,766 B1 | Page 1 of 1 |
| DATED | : November 13, 2001 | |
| INVENTOR(S) | : Solgun Drevik | |

It is certified that error appears in the above-identified patent and that said Letters Patent is hereby corrected as shown below:

<u>Title page,</u>
Item [73] Assignee, please delete "SGA" and insert therefor -- SCA --.

Signed and Sealed this

Third Day of September, 2002

Attest:

Attesting Officer

JAMES E. ROGAN
*Director of the United States Patent and Trademark Office*